US00PP28570P2

(12) United States Plant Patent
Korlipara

(10) Patent No.: US PP28,570 P2
(45) Date of Patent: Oct. 24, 2017

(54) ***COREOPSIS* PLANT NAMED 'MADRAS MAGIC'**

(50) Latin Name: ***Coreopsis verticillata* hybrid**
Varietal Denomination: Madras Magic

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/330,201

(22) Filed: Aug. 22, 2016

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Klarquist Sparkman, LLP

(57) ABSTRACT

A new and distinct *Coreopsis* plant named 'Madras Magic' characterized by daisy-type inflorescences that grow to 4 cm in diameter, inflorescences that are dark rose burgundy with streaks of creamy white near the tips, hardy to Zone 6, maybe lower, grass green foliage on short stems, flowering for the whole summer, a low, mounding habit, and excellent vigor.

1 Drawing Sheet

Latin name: *Coreopsis verticillata* hybrid.
Varietal denomination: 'Madras Magic'.

BACKGROUND OF THE INVENTION

The present invention relates to a new and distinct *Coreopsis* and given the cultivar name 'Madras Magic'. *Coreopsis* is in the family Asteraceae. This new cultivar originated from a controlled breeding program to produce hardy compact *Coreopsis*. The new cultivar originated from planned cross of two proprietary unnamed *Coreopsis verticillata* hybrid seedlings. The new cultivar of *Coreopsis* is an herbaceous perennial to be grown for landscape and container use in a sunny site.

Compared to the parent seedlings the new variety is much shorter with larger flowers and a more upright habit.

Compared to *Coreopsis* 'Show Stopper', U.S. Plant Pat. No. 22,671, the new cultivar is much shorter and much more compact.

Compared to *Coreopsis* 'Cosmic Evolution', U.S. Plant Pat. No. 22,9453, the new cultivar is smaller and more compact and has smaller, darker flowers.

Compared to *Coreopsis* 'Mercury Rising', U.S. Plant Pat. No. 24,689, the new cultivar has a tighter more compact habit and flowers that are a dark rose burgundy rather than red.

SUMMARY OF THE INVENTION

The following traits have been repeatedly observed and are determined to be the unique characteristics of the new variety. These characteristics in combination distinguish *Coreopsis* 'Madras Magic' as a new and distinct cultivar:

1. daisy-type inflorescences that grow to 4 cm in diameter,
2. inflorescences that are dark rose burgundy with streaks of creamy white near the tips,
3. hardy to Lone 6, maybe lower,
4. grass green foliage on short stems, 5. flowering for the whole summer,
6. a low, mounding habit, and
7. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a nine-month-old *Coreopsis* 'Madras Magic' growing in the ground in the trial field in July in Canby, Oreg.

FIG. 2 shows a close up of the flowers.

DETAILED PLANT DESCRIPTION

The following is a detailed description of the new *Coreopsis* cultivar based on observations of nine-month-old specimens growing in one gallon containers in full sun in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart*, 5$^{th}$ edition, 2007.

Plant:

*Type*.—Herbaceous perennial.

*Hardiness*.—USDA Zones 6 to 9.

*Size*.—45 cm wide and 37 cm tall to top of inflorescences.

*Form*.—Mound.
*Vigor*.—Excellent.
*Roots*.—Fibrous, stems root easily from stem cuttings.

Stem:
*Type*.—Ascending, well branched.
*Size*.—Grows to 24 cm tall and 8 mm wide.
*Number of stems from the crown*.—5.
*Branching habit*.—Freely branched, an average of 7 paired lateral branches with secondary branches, branches are opposite in arrangement, new lateral flowering branches are continuously produced throughout the summer.
*Internode length*.—1 cm to 3.5 cm.
*Surface*.—Minutely glandular.
*Color*.—Brown 200A at bottom 7 cm blending to Yellow Green 147B.

Leaf:
*Type*.—Simple.
*Shape*.—Pinnately 3-parted into thread-like segments to linear on top leaves.
*Arrangement*.—Opposite.
*Size*.—Grow to 8.5 cm wide and 9.5 cm long; the terminal linear segment can grow to 42 mm long and 2 mm wide, laterals can grow to 35 mm long and 2 mm wide.
*Apex*.—Acute.
*Margins*.—Entire.
*Petiole*.—0 mm to 1.5 mm long and 1.5 mm wide, Green 137A.
*Surface texture*.—Sparsely pubescent on top and minutely glandular on bottom side.
*Venation*.—Pinnate, visible main vein the same color as the leaf on both sides.
*Color*.—Topside Green N137A, bottom side Green N137B.

Inflorescence:
*Type*.—Long stalked terminal heads of daisy type inflorescences.
*Peduncle*.—Grows to 7.5 cm long, 1 mm wide, glabrous, Green 137A.
*Size*.—Grows to 4 cm wide and 8 mm deep.
*Immature* (*bud*).—Globular, 7 mm wide and 8 mm deep, Yellow Green 138A, glabrous.
*Receptacle*.—Disc shaped, 3 mm wide and 1.5 mm deep, Green 148B.
*Phyllaries*.—In 2 series; first series closet to ray florets in an area 5 mm deep and spreading 12 wide mm, 8 in number, each 6 mm long and 3 mm wide, lanceolate, margin entire, tip acute, glabrous on both sides, both sides Yellow Orange 16A on top ½ blending to 138A on bottom ⅔; lower series in an area 3 mm deep and 8 mm wide, 8 linear lobes, each 3 mm long and 1.5 mm wide, margin entire, tip acute, top side glandular, bottom side glabrous, both sides Green 137A.
*Self-cleaning*.—Yes.
*Lastingness*.—Each inflorescence lasts about a week on the plant.

Florets:
*Type*.—Composite.
*Ray florets*.—8 in number with no pistil or stamen, grows to 22 mm long, 8 mm wide, obovate, with the tip obtuse to 2 notched, margins entire, glabrous on both sides; topside Purple N79B on bottom half blending to streaks of White 155A on top half, bottom side Greyed Brown 199D (where purple on top) to Yellow 4D (where White of top).
*Disc*.—Flat becoming rounded with maturity, 9 mm wide and becoming 5 mm deep with maturity, Orange 22A.
*Disc florets*.—Tubular, with stamen and pistil, about 90 in number, 8 mm long and 1 mm wide, tubular; corolla 5 mm long, 5 lobed, tube Yellow 13B, lobes Greyed Purple 187A; pistil 1, 8 mm long, ovary 3 mm long, Green Yellow 1C, style 4 mm long, with extruding, 2-branched stigma, stigma and style Yellow Orange 22A; stamen 5, anthers 1.2 mm long, Greyed Brown N199B, pollen none.
*Bloom period*.—June through frost in Canby, Oreg.
*Fragrance*.—No noticeable.
*Seed*.—None seen.
*Fertility*.—Unknown.

Disease and pests: No pests or diseases have been observed on plants grown under commercial conditions in Canby, Oreg. No resistances are known.

I claim:

1. A new and distinct *Coreopsis* plant as herein illustrated and described.

* * * * *

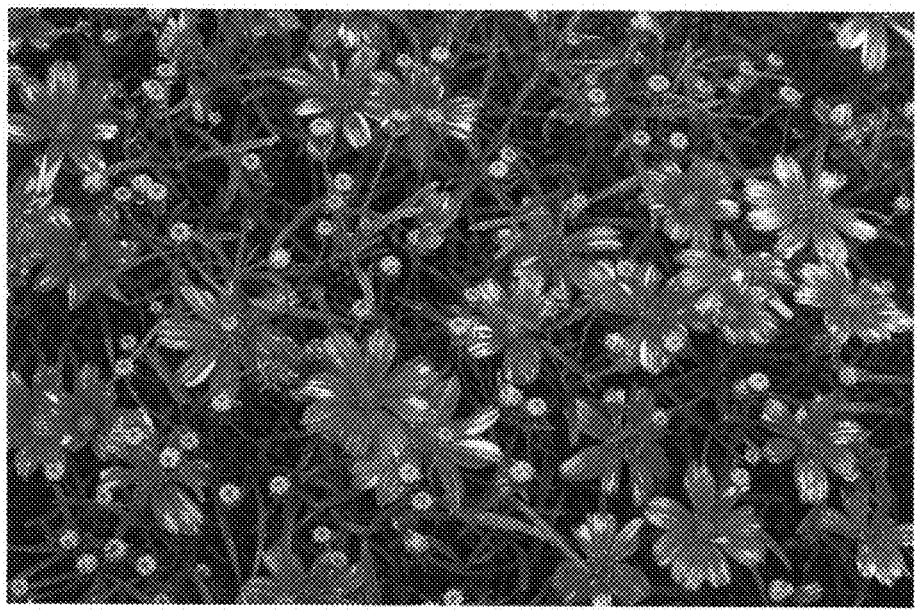

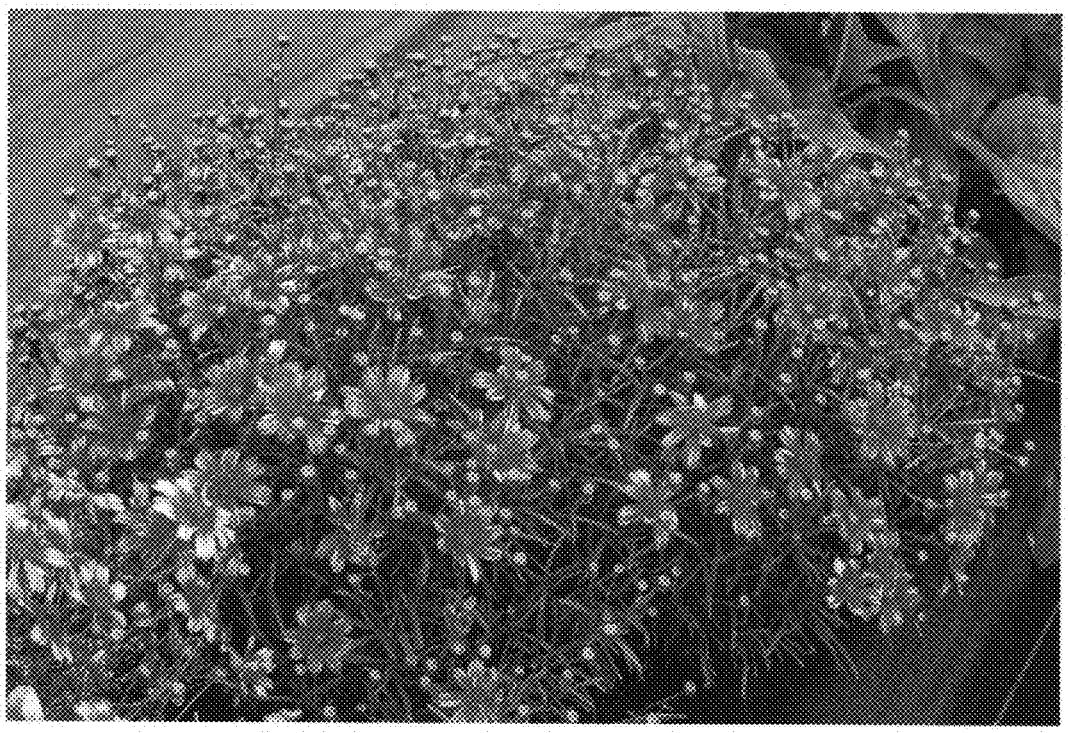
FIG. 1 above, FIG. 2 below